(12) United States Patent
Liu

(10) Patent No.: US 11,266,832 B2
(45) Date of Patent: Mar. 8, 2022

(54) ELECTROPHORETIC ACTIVE DELIVERY SYSTEM INCLUDING POROUS CONDUCTIVE ELECTRODE LAYER

(71) Applicant: E Ink California, LLC, Fremont, CA (US)

(72) Inventor: Lei Liu, Fremont, CA (US)

(73) Assignee: E INK CALIFORNIA, LLC, Fremont, CA (US)

( * ) Notice: Subject to any disclaimer, the term of this patent is extended or adjusted under 35 U.S.C. 154(b) by 624 days.

(21) Appl. No.: 16/186,808

(22) Filed: Nov. 12, 2018

(65) Prior Publication Data

US 2019/0143105 A1 May 16, 2019

Related U.S. Application Data

(60) Provisional application No. 62/585,663, filed on Nov. 14, 2017.

(51) Int. Cl.
| | | |
|---|---|---|
| *A61N 1/32* | (2006.01) | |
| *A61N 1/04* | (2006.01) | |
| *A61K 9/70* | (2006.01) | |

(52) U.S. Cl.
CPC ............ *A61N 1/327* (2013.01); *A61K 9/7092* (2013.01); *A61N 1/044* (2013.01); *A61N 1/0428* (2013.01); *A61N 1/0448* (2013.01); *A61N 1/325* (2013.01); *A61N 1/0476* (2013.01)

(58) Field of Classification Search
CPC ................ A61N 1/0476; A61N 1/0448; A61N 1/0432–0444; A61K 9/7092
See application file for complete search history.

(56) References Cited

U.S. PATENT DOCUMENTS

| | | |
|---|---|---|
| 3,756,693 A | 9/1973 | Ota |
| 3,892,568 A | 7/1975 | Ota |
| 4,298,448 A | 11/1981 | Muller et al. |
| 4,559,222 A | 12/1985 | Enscore et al. |
| 4,640,689 A | 2/1987 | Sibalis |
| 4,734,090 A | 3/1988 | Sibalis |

(Continued)

FOREIGN PATENT DOCUMENTS

| | | |
|---|---|---|
| CN | 1705907 A | 12/2005 |
| EP | 1457233 A1 | 9/2004 |

(Continued)

OTHER PUBLICATIONS

"Magetically Triggered Reversible Controlled Drug Deliveyr form Microfabricated Polymeric Multireservoir Devices", Cai et al., 2009. Advanced Materials. 21 (4045-4049).*

(Continued)

*Primary Examiner* — Bhisma Mehta
*Assistant Examiner* — John J Crawford
(74) *Attorney, Agent, or Firm* — Ioannis Constantinides

(57) ABSTRACT

An active molecule delivery system whereby active molecules can be released on demand and/or a variety of different active molecules can be delivered from the same system and/or different concentrations of active molecules can be delivered from the same system. The active molecule delivery system includes a first electrode, a plurality of microcells, and a porous conductive layer. The microcells are filled with a medium including active molecules.

19 Claims, 11 Drawing Sheets

(56) References Cited

U.S. PATENT DOCUMENTS

| | | | |
|---|---|---|---|
| 5,125,894 | A | 6/1992 | Phipps et al. |
| 5,135,479 | A | 8/1992 | Sibalis et al. |
| 5,378,574 | A | 1/1995 | Winnik et al. |
| 5,486,362 | A | 1/1996 | Kitchell et al. |
| 5,533,995 | A | 7/1996 | Corish et al. |
| 5,591,767 | A | 1/1997 | Mohr et al. |
| 5,603,693 | A | 2/1997 | Frenkel et al. |
| 5,658,592 | A | 8/1997 | Tanihara et al. |
| 5,797,898 | A | 8/1998 | Santini, Jr. et al. |
| 5,931,804 | A | 8/1999 | Sibalis |
| 5,980,719 | A | 11/1999 | Cherukuri et al. |
| 5,980,943 | A | 11/1999 | Ayer et al. |
| 6,017,584 | A | 1/2000 | Albert et al. |
| 6,123,861 | A | 9/2000 | Santini, Jr. et al. |
| 6,198,809 | B1 | 3/2001 | DiSanto et al. |
| 6,337,761 | B1 | 1/2002 | Rogers et al. |
| 6,373,461 | B1 | 4/2002 | Hasegawa et al. |
| 6,486,866 | B1 | 11/2002 | Kuwahara et al. |
| 6,491,666 | B1 | 12/2002 | Santini, Jr. et al. |
| 6,517,618 | B2 | 2/2003 | Foucher et al. |
| 6,521,191 | B1 | 2/2003 | Schenk et al. |
| 6,525,866 | B1 | 2/2003 | Lin et al. |
| 6,538,801 | B2 | 3/2003 | Jacobson et al. |
| 6,545,797 | B2 | 4/2003 | Chen et al. |
| 6,564,093 | B1 | 5/2003 | Ostrow et al. |
| 6,565,532 | B1 | 5/2003 | Yuzhakov et al. |
| 6,600,534 | B1 | 7/2003 | Tanaka et al. |
| 6,650,462 | B2 | 11/2003 | Katase |
| 6,664,944 | B1 | 12/2003 | Albert et al. |
| 6,680,726 | B2 | 1/2004 | Gordon, II et al. |
| 6,693,620 | B1 | 2/2004 | Herb et al. |
| 6,704,133 | B2 | 3/2004 | Gates et al. |
| 6,724,521 | B2 | 4/2004 | Nakao et al. |
| 6,729,718 | B2 | 5/2004 | Goto et al. |
| 6,751,007 | B2 | 6/2004 | Liang et al. |
| 6,751,008 | B2 | 6/2004 | Liang et al. |
| 6,757,560 | B1 | 6/2004 | Fischer et al. |
| 6,781,745 | B2 | 8/2004 | Chung et al. |
| 6,788,452 | B2 | 9/2004 | Liang et al. |
| 6,829,078 | B2 | 12/2004 | Liang et al. |
| 6,850,357 | B2 | 2/2005 | Kaneko et al. |
| 6,864,875 | B2 | 3/2005 | Drzaic et al. |
| 6,876,486 | B2 | 4/2005 | Hiraoka et al. |
| 6,914,714 | B2 | 7/2005 | Chen et al. |
| 6,930,818 | B1 | 8/2005 | Liang et al. |
| 6,933,098 | B2 | 8/2005 | Chan-Park et al. |
| 6,947,203 | B2 | 9/2005 | Kanbe |
| 6,967,762 | B2 | 11/2005 | Machida et al. |
| 6,972,893 | B2 | 12/2005 | Chen et al. |
| 6,980,855 | B2 | 12/2005 | Cho |
| 6,987,503 | B2 | 1/2006 | Inoue |
| 6,987,605 | B2 | 1/2006 | Liang et al. |
| 7,009,756 | B2 | 3/2006 | Kishi et al. |
| 7,019,889 | B2 | 3/2006 | Katase |
| 7,034,987 | B2 | 4/2006 | Schlangen |
| 7,038,655 | B2 | 5/2006 | Herb et al. |
| 7,038,656 | B2 | 5/2006 | Liang et al. |
| 7,038,670 | B2 | 5/2006 | Liang et al. |
| 7,046,228 | B2 | 5/2006 | Liang et al. |
| 7,050,218 | B2 | 5/2006 | Kanbe |
| 7,052,571 | B2 | 5/2006 | Wang et al. |
| 7,057,600 | B2 | 6/2006 | Goden |
| 7,057,798 | B2 | 6/2006 | Ukigaya |
| 7,075,502 | B1 | 7/2006 | Drzaic et al. |
| 7,116,466 | B2 | 10/2006 | Whitesides et al. |
| 7,167,155 | B1 | 1/2007 | Albert et al. |
| 7,226,550 | B2 | 6/2007 | Hou et al. |
| 7,229,556 | B1 | 6/2007 | Hinds, III et al. |
| 7,259,744 | B2 | 8/2007 | Arango et al. |
| 7,271,947 | B2 | 9/2007 | Liang et al. |
| 7,279,064 | B2 | 10/2007 | Daniel et al. |
| 7,283,119 | B2 | 10/2007 | Kishi |
| 7,292,386 | B2 | 11/2007 | Kanbe |
| 7,303,818 | B2 | 12/2007 | Minami |
| 7,304,987 | B1 | 12/2007 | James et al. |
| 7,312,916 | B2 | 12/2007 | Pullen et al. |
| 7,315,758 | B2 | 1/2008 | Kwiatkowski et al. |
| 7,342,556 | B2 | 3/2008 | Oue et al. |
| 7,345,810 | B2 | 3/2008 | Chopra et al. |
| 7,352,353 | B2 | 4/2008 | Albert et al. |
| 7,365,732 | B2 | 4/2008 | Matsuda et al. |
| 7,382,351 | B2 | 6/2008 | Kishi |
| 7,383,083 | B2 * | 6/2008 | Fischer .................. A61N 1/044 604/20 |
| 7,385,751 | B2 | 6/2008 | Chen et al. |
| 7,392,080 | B2 | 6/2008 | Eppstein et al. |
| 7,411,719 | B2 | 8/2008 | Paolini, Jr. et al. |
| 7,417,787 | B2 | 8/2008 | Chopra et al. |
| 7,420,549 | B2 | 9/2008 | Jacobson et al. |
| 7,433,113 | B2 | 10/2008 | Chopra et al. |
| 7,443,570 | B2 | 10/2008 | Chopra et al. |
| 7,474,295 | B2 | 1/2009 | Matsuda |
| 7,492,505 | B2 | 2/2009 | Liang et al. |
| 7,495,821 | B2 | 2/2009 | Yamakita et al. |
| 7,502,162 | B2 | 3/2009 | Lin et al. |
| 7,537,590 | B2 | 5/2009 | Santini, Jr. et al. |
| 7,545,557 | B2 | 6/2009 | Iftime et al. |
| 7,548,291 | B2 | 6/2009 | Lee et al. |
| 7,557,981 | B2 | 7/2009 | Liang et al. |
| 7,580,025 | B2 | 8/2009 | Nakai et al. |
| 7,604,628 | B2 | 10/2009 | Santini, Jr. et al. |
| 7,605,972 | B2 | 10/2009 | Kawai et al. |
| 7,609,435 | B2 | 10/2009 | Moriyama et al. |
| 7,611,481 | B2 | 11/2009 | Cleary et al. |
| 7,626,185 | B2 | 12/2009 | Krak et al. |
| 7,636,076 | B2 | 12/2009 | Hung et al. |
| 7,652,656 | B2 | 1/2010 | Chopra et al. |
| 7,656,576 | B2 | 2/2010 | Suwabe et al. |
| 7,667,684 | B2 | 2/2010 | Jacobson et al. |
| 7,679,599 | B2 | 3/2010 | Kawai |
| 7,684,108 | B2 | 3/2010 | Wang et al. |
| 7,686,463 | B2 | 3/2010 | Goto |
| 7,715,088 | B2 | 5/2010 | Liang et al. |
| 7,760,419 | B2 | 7/2010 | Lee |
| 7,782,292 | B2 | 8/2010 | Miyasaka et al. |
| 7,791,789 | B2 | 9/2010 | Albert et al. |
| 7,800,813 | B2 | 9/2010 | Wu et al. |
| 7,808,696 | B2 | 10/2010 | Lee et al. |
| 7,821,702 | B2 | 10/2010 | Liang et al. |
| 7,830,592 | B1 | 11/2010 | Sprague et al. |
| 7,839,564 | B2 | 11/2010 | Whitesides et al. |
| 7,848,009 | B2 | 12/2010 | Machida et al. |
| 7,852,547 | B2 | 12/2010 | Kim |
| 7,852,548 | B2 | 12/2010 | Roh |
| 7,892,221 | B2 | 2/2011 | Santini, Jr. et al. |
| 7,907,327 | B2 | 3/2011 | Jang et al. |
| 7,910,175 | B2 | 3/2011 | Webber |
| 7,911,681 | B2 | 3/2011 | Ikegami et al. |
| 7,952,790 | B2 | 5/2011 | Honeyman |
| 7,956,841 | B2 | 6/2011 | Albert et al. |
| 7,982,941 | B2 | 7/2011 | Lin et al. |
| 8,040,594 | B2 | 10/2011 | Paolini, Jr. et al. |
| 8,054,526 | B2 | 11/2011 | Bouchard |
| 8,067,305 | B2 | 11/2011 | Zafiropoulo et al. |
| 8,072,675 | B2 | 12/2011 | Lin et al. |
| 8,081,375 | B2 | 12/2011 | Komatsu et al. |
| 8,089,686 | B2 | 1/2012 | Addington et al. |
| 8,095,213 | B1 | 1/2012 | Sexton |
| 8,098,418 | B2 | 1/2012 | Paolini, Jr. et al. |
| 8,115,729 | B2 | 2/2012 | Danner et al. |
| 8,120,838 | B2 | 2/2012 | Lin et al. |
| 8,159,636 | B2 | 4/2012 | Sun et al. |
| 8,164,823 | B2 | 4/2012 | Ikegami et al. |
| 8,169,690 | B2 | 5/2012 | Lin et al. |
| 8,174,492 | B2 | 5/2012 | Kim et al. |
| 8,213,076 | B2 | 7/2012 | Albert et al. |
| 8,237,892 | B1 | 8/2012 | Sprague et al. |
| 8,243,013 | B1 | 8/2012 | Sprague et al. |
| 8,257,324 | B2 | 9/2012 | Prausnitz et al. |
| 8,355,196 | B2 | 1/2013 | Yan et al. |
| 8,363,299 | B2 | 1/2013 | Paolini, Jr. et al. |
| 8,395,836 | B2 | 3/2013 | Lin |
| 8,403,915 | B2 | 3/2013 | Santini, Jr. et al. |
| 8,422,116 | B2 | 4/2013 | Sprague et al. |

(56) References Cited

U.S. PATENT DOCUMENTS

| | | |
|---|---|---|
| 8,440,222 B2 | 5/2013 | Hausner et al. |
| 8,441,713 B2 | 5/2013 | Kawashima et al. |
| 8,441,714 B2 | 5/2013 | Paolini, Jr. et al. |
| 8,441,716 B2 | 5/2013 | Paolini, Jr. et al. |
| 8,466,852 B2 | 6/2013 | Drzaic et al. |
| 8,477,404 B2 | 7/2013 | Moriyama et al. |
| 8,477,405 B2 | 7/2013 | Ishii et al. |
| 8,503,063 B2 | 8/2013 | Sprague |
| 8,517,958 B2 | 8/2013 | Eppstein et al. |
| 8,520,296 B2 | 8/2013 | Wang et al. |
| 8,537,104 B2 | 9/2013 | Markvoort et al. |
| 8,565,522 B2 | 10/2013 | Swic |
| 8,570,272 B2 | 10/2013 | Hsieh et al. |
| 8,570,639 B2 | 10/2013 | Masuzawa et al. |
| 8,574,937 B2 | 11/2013 | Shi |
| 8,576,470 B2 | 11/2013 | Paolini, Jr. et al. |
| 8,576,475 B2 | 11/2013 | Huang et al. |
| 8,593,721 B2 | 11/2013 | Albert et al. |
| 8,599,120 B2 | 12/2013 | Kanou |
| 8,605,354 B2 | 12/2013 | Zhang et al. |
| 8,610,998 B2 | 12/2013 | Baisch et al. |
| 8,629,832 B2 | 1/2014 | Tanabe |
| 8,649,084 B2 | 2/2014 | Wang et al. |
| 8,670,174 B2 | 3/2014 | Sprague et al. |
| 8,674,978 B2 | 3/2014 | Komatsu et al. |
| 8,681,191 B2 | 3/2014 | Yang et al. |
| 8,687,265 B2 | 4/2014 | Ahn et al. |
| 8,696,637 B2 | 4/2014 | Ross |
| 8,704,754 B2 | 4/2014 | Machida et al. |
| 8,704,756 B2 | 4/2014 | Lin |
| 8,717,662 B2 | 5/2014 | Komatsu |
| 8,717,664 B2 | 5/2014 | Wang et al. |
| 8,744,569 B2 | 6/2014 | Imran |
| 8,786,935 B2 | 7/2014 | Sprague |
| 8,797,258 B2 | 8/2014 | Sprague |
| 8,797,634 B2 | 8/2014 | Paolini, Jr. et al. |
| 8,797,636 B2 | 8/2014 | Yang et al. |
| 8,797,637 B2 | 8/2014 | Fujishiro et al. |
| 8,810,899 B2 | 8/2014 | Sprague et al. |
| 8,830,559 B2 | 9/2014 | Honeyman et al. |
| 8,830,561 B2 | 9/2014 | Zang et al. |
| 8,862,223 B2 | 10/2014 | Yanaki |
| 8,873,129 B2 | 10/2014 | Paolini, Jr. et al. |
| 8,902,153 B2 | 12/2014 | Bouchard et al. |
| 8,902,491 B2 | 12/2014 | Wang et al. |
| 8,917,439 B2 | 12/2014 | Wang et al. |
| 8,962,014 B2 | 2/2015 | Prinz et al. |
| 8,964,282 B2 | 2/2015 | Wang et al. |
| 8,968,699 B2 | 3/2015 | Jin et al. |
| 8,976,444 B2 | 3/2015 | Zhang et al. |
| 9,013,783 B2 | 4/2015 | Sprague |
| 9,052,564 B2 | 6/2015 | Sprague et al. |
| 9,116,412 B2 | 8/2015 | Lin |
| 9,140,952 B2 | 9/2015 | Sprague et al. |
| 9,146,439 B2 | 9/2015 | Zhang |
| 9,164,207 B2 | 10/2015 | Honeyman et al. |
| 9,170,467 B2 | 10/2015 | Whitesides et al. |
| 9,170,468 B2 | 10/2015 | Lin et al. |
| 9,182,646 B2 | 11/2015 | Paolini, Jr. et al. |
| 9,186,317 B2 | 11/2015 | Smyth et al. |
| 9,188,829 B2 | 11/2015 | Li et al. |
| 9,195,111 B2 | 11/2015 | Anseth et al. |
| 9,199,441 B2 | 12/2015 | Danner |
| 9,251,736 B2 | 2/2016 | Lin et al. |
| 9,268,191 B2 | 2/2016 | Paolini, Jr. et al. |
| 9,285,649 B2 | 3/2016 | Du et al. |
| 9,293,511 B2 | 3/2016 | Jacobson et al. |
| 9,320,720 B2 | 4/2016 | Maier |
| 9,326,979 B2 | 5/2016 | Kimura et al. |
| 9,327,105 B2 | 5/2016 | Ramdas et al. |
| 9,341,916 B2 | 5/2016 | Telfer et al. |
| 9,360,733 B2 | 6/2016 | Wang et al. |
| 9,361,836 B1 | 6/2016 | Telfer et al. |
| 9,383,623 B2 | 7/2016 | Lin et al. |
| 9,388,307 B2 * | 7/2016 | Li .................. B32B 7/06 |
| 9,423,666 B2 | 8/2016 | Wang et al. |
| 9,459,510 B2 | 10/2016 | Lin |
| 9,460,666 B2 | 10/2016 | Sprague et al. |
| 9,513,527 B2 | 12/2016 | Chan et al. |
| 9,541,814 B2 | 1/2017 | Lin et al. |
| 9,610,440 B2 | 4/2017 | Jordan et al. |
| 9,671,668 B2 | 6/2017 | Chan et al. |
| 9,697,778 B2 | 7/2017 | Telfer et al. |
| 9,740,076 B2 | 8/2017 | Paolini, Jr. et al. |
| 9,759,980 B2 | 9/2017 | Du et al. |
| 9,812,073 B2 | 11/2017 | Lin et al. |
| 9,931,296 B2 | 4/2018 | Doshi |
| 9,968,549 B2 | 5/2018 | Kosel et al. |
| 10,036,931 B2 | 7/2018 | Chan et al. |
| 10,162,242 B2 | 12/2018 | Wang et al. |
| 10,209,556 B2 | 2/2019 | Rosenfeld et al. |
| 10,332,435 B2 | 6/2019 | Wang et al. |
| 10,514,583 B2 | 12/2019 | Zhang |
| 10,646,454 B2 | 5/2020 | Liu et al. |
| 10,918,846 B2 | 2/2021 | Nagai et al. |
| 10,933,029 B2 | 3/2021 | Liu |
| 2001/0023330 A1 * | 9/2001 | Palti .................. A61N 1/325 604/20 |
| 2001/0035926 A1 | 11/2001 | Yamaguchi et al. |
| 2004/0085619 A1 | 5/2004 | Wu et al. |
| 2005/0191337 A1 | 9/2005 | Gueret |
| 2006/0009731 A1 | 1/2006 | Wu et al. |
| 2006/0257450 A1 | 11/2006 | Mudumba et al. |
| 2006/0269475 A1 | 11/2006 | Ryu et al. |
| 2007/0002008 A1 | 1/2007 | Tam |
| 2007/0080928 A1 | 4/2007 | Ishii et al. |
| 2007/0083186 A1 * | 4/2007 | Carter .................. A61N 1/044 604/501 |
| 2007/0196456 A1 | 8/2007 | Stevens et al. |
| 2007/0248657 A1 | 10/2007 | Smith et al. |
| 2007/0273637 A1 | 11/2007 | Zhou et al. |
| 2007/0292463 A1 | 12/2007 | Spector |
| 2008/0020007 A1 * | 1/2008 | Zang .................. G02F 1/133377 424/401 |
| 2008/0042928 A1 | 2/2008 | Schlangen et al. |
| 2008/0043318 A1 | 2/2008 | Whitesides et al. |
| 2008/0048970 A1 | 2/2008 | Drzaic et al. |
| 2008/0062159 A1 | 3/2008 | Roh et al. |
| 2008/0117165 A1 | 5/2008 | Machida et al. |
| 2008/0174531 A1 | 7/2008 | Sah |
| 2009/0153942 A1 | 6/2009 | Daniel et al. |
| 2009/0167754 A1 | 7/2009 | Hatta |
| 2009/0184897 A1 | 7/2009 | Miyamoto |
| 2009/0225398 A1 | 9/2009 | Duthaler et al. |
| 2009/0234214 A1 | 9/2009 | Santini, Jr. et al. |
| 2009/0311484 A1 | 12/2009 | Mclellan et al. |
| 2010/0030129 A1 | 2/2010 | Nitzan et al. |
| 2010/0156780 A1 | 6/2010 | Jacobson et al. |
| 2010/0189793 A1 * | 7/2010 | Meyer .................. A61N 1/044 424/484 |
| 2010/0331811 A1 * | 12/2010 | Imran .................. A61N 1/0428 604/501 |
| 2011/0043543 A1 | 2/2011 | Chen et al. |
| 2011/0046557 A1 | 2/2011 | Lee et al. |
| 2011/0111013 A1 | 5/2011 | Salman et al. |
| 2011/0175939 A1 | 7/2011 | Moriyama et al. |
| 2011/0196474 A1 | 8/2011 | Davalian et al. |
| 2011/0199671 A1 | 8/2011 | Amundson et al. |
| 2011/0217639 A1 | 9/2011 | Sprague |
| 2011/0234557 A1 | 9/2011 | Yang et al. |
| 2012/0299947 A1 | 11/2012 | Tsuda et al. |
| 2012/0326957 A1 | 12/2012 | Drzaic et al. |
| 2013/0096486 A1 | 4/2013 | Schroeder et al. |
| 2013/0242378 A1 | 9/2013 | Paolini, Jr. et al. |
| 2013/0278995 A1 | 10/2013 | Drzaic et al. |
| 2014/0009818 A1 | 1/2014 | Brochon et al. |
| 2014/0011913 A1 | 1/2014 | Du et al. |
| 2014/0055840 A1 | 2/2014 | Zang et al. |
| 2014/0078576 A1 | 3/2014 | Sprague |
| 2014/0330223 A1 | 11/2014 | Schurad et al. |
| 2014/0362213 A1 | 12/2014 | Tseng |
| 2015/0005720 A1 | 1/2015 | Zang |
| 2015/0018749 A1 * | 1/2015 | Faupel .................. A61K 9/7084 604/20 |

(56) References Cited

U.S. PATENT DOCUMENTS

| | | |
|---|---|---|
| 2015/0118390 A1 | 4/2015 | Rosenfeld et al. |
| 2015/0167184 A1 | 6/2015 | Abhishek et al. |
| 2015/0241754 A1 | 8/2015 | Du et al. |
| 2015/0268531 A1 | 9/2015 | Wang et al. |
| 2015/0301246 A1 | 10/2015 | Zang et al. |
| 2015/0301425 A1 | 10/2015 | Du et al. |
| 2016/0045158 A1 | 2/2016 | Hsu |
| 2016/0048054 A1 | 2/2016 | Danner |
| 2016/0279072 A1 | 9/2016 | Li et al. |
| 2017/0121563 A1 | 5/2017 | Moran |
| 2017/0205649 A1 | 7/2017 | Wang et al. |
| 2018/0271799 A1 | 9/2018 | Liu et al. |
| 2018/0271800 A1 | 9/2018 | Liu et al. |
| 2018/0272114 A1 | 9/2018 | Liu et al. |
| 2019/0142763 A1 | 5/2019 | Liu |
| 2019/0143105 A1 | 5/2019 | Liu |

FOREIGN PATENT DOCUMENTS

| | | | |
|---|---|---|---|
| JP | 2006343458 | A | 12/2006 |
| JP | 2007033710 | A | 2/2007 |
| JP | 2008033000 | A | 2/2008 |
| JP | 2008209589 | A | 9/2008 |
| JP | 2009116041 | A | 5/2009 |
| JP | 2009192637 | A | 8/2009 |
| JP | 2009244635 | A | 10/2009 |
| JP | 2010044114 | A | 2/2010 |
| JP | 2010210856 | A | 9/2010 |
| JP | 2011158783 | A | 8/2011 |
| KR | 19980025307 | A | 7/1998 |
| KR | 20070082680 | A | 8/2007 |
| KR | 20110103765 | A | 9/2011 |
| KR | 20190122531 | A | 10/2019 |
| TW | 201122697 | A | 7/2011 |
| TW | 201237529 | A | 9/2012 |
| WO | 1999053373 | A1 | 10/1999 |
| WO | 2009073686 | A1 | 6/2009 |

OTHER PUBLICATIONS

Seigou Kawaguchi et al., "Synthesis of polyethylene macromonomers and their radical copolymerizations with methyl methacrylate in homogeneous and oligoethylene melts media" Designed Monomers and Polymers 2000, vol. 3, No. 3, p. 263-277 Jan. 1, 2000.
Korean Intellectual Property Office; PCT/US2015/011237; International Search Report and Written Opinion ; dated Apr. 10, 2015, dated Apr. 10, 2015.
European Patent Office; EP Appl. No. 15737734.2; Extended European Search Report; dated Jun. 6, 2017, dated Jun. 6, 2017.
European Patent Office, EP. Appl. No. 18772394.5, European Search Report, dated Nov. 30, 2020, dated Nov. 30, 2020.
European Patent Office, EP. Appl. No. 18771792.1, Supplemental Partial European Search Report, dated Nov. 24, 2020, dated Nov. 24, 2020.
European Patent Office, EP Appl. No. 18878337.7, Extended European Search Report, dated Feb. 8, 2021, dated Feb. 8, 2021.
Korean Intellectual Property Office, PCT/US2020/061253, International Search Report and Written Opinion, dated Mar. 9, 2021, dated Mar. 9, 2021.
European Patent Office, EP. Appl. No. 18771792.1, Extended European Search Report, dated Nov. 24, 2020, dated Mar. 31, 2021.
Harvey, T.G.; "Replication techniques for micro-optics"; SPIE Proc. vol. 3099, pp. 76-82; 1997.
Korean Intellectual Property Office, PCT/US2018/060259, International Search Report and Written Opinion, dated Apr. 29, 2019, dated Apr. 29, 2019.
Ebbert Jon O. et al., "Combination Pharmacotherapy for Stopping Smoking: What Advantages Does it Offer?", Drugs, vol. 70 No. 6, pp. 643-650, (Apr. 16, 2010). Apr. 16, 2010.
Kaiyong Cai et al., "Magnetically triggered reversible Controlled Drug Delivery from Microfabricated Polymeric Multireservior Devices"., Advanced Materials. 2009, 21, 4045-4049 May 28, 2009.
Korean Intellectual Property Office, PCT/US2018/023917, International Search Report and Written Opinion, dated Jul. 10, 2017, dated Jul. 10, 2018.
Korean Intellectual Property Office, PCT/US2018/023928, International Search Report and Written Opinion, dated Jul. 10, 2018, dated Jul. 10, 2018.
Korean Intellectual Property Office, PCT/US2018/023921, International Search Report and Written Opinion, dated Jul. 10, 2018, dated Jul. 10, 2018.
Korean Intellectual Property Office, PCT/US2018/060266, International Search Report and Written Opinion, dated Apr. 29, 2019, dated Apr. 29, 2019.
Xuan, Shouhu et al., "Systhesis of Fe3O4@Polyaniline Core/Shell Microspheres with Well-Defined Blackberrym-Like Morphology", J. Phys. Chem. C., vol. 112, pp. 18804-18809. (2008). Oct. 3, 2008.
Sahoo et al., "A Review of Transdermal drug delivery system", Journal der Pharmazie Forschung, vol. 2, N-1, 2013, 32-56 (2013) 2013.
Huang, W. C. et al . . . , "A flexible drug delivery chip for the magnetically-controlled release of anti-epileptic drugs", Journal of Controlled Release, vol. 139, Issue 3, Nov. 3, 2009, pp. 221-228.
European Patent Office, EP Appl. No. 18771343.3, Extended European Search Report, dated Aug. 14, 2020, dated Aug. 14, 2020.
Gulati Gaurav Kumar et al., "Programmable carbon nanotube membrane-based transdermal nicotine delivery with microdialysis validation assay", Nanomedicine: Nanotechnology, Biology and medicine, Elsevier, NL, vol. 13, No. 1, Jul. 18, 2016, p. 1-9, XP029879755, ISSN: 1549-9634 (Jul. 18, 2016) Jul. 18, 2016.
Im J S et al., "The effect of carbon nanotubes on drug delivery in an electro-sensitive transdermal drug delivery system" Biomaterials, Elsevier, Amsterdam, NL, vol. 31, No. 6, Feb. 1, 2010, pp. 1414-1419, XP026814171, ISSN: 0142-9612 ( Feb. 1, 2020) Feb. 1, 2010.
European Patent Office, "European Search Report", EP Appl. No. 18879750.0, dated Jul. 27, 2021, dated Jul. 27, 2021.

\* cited by examiner

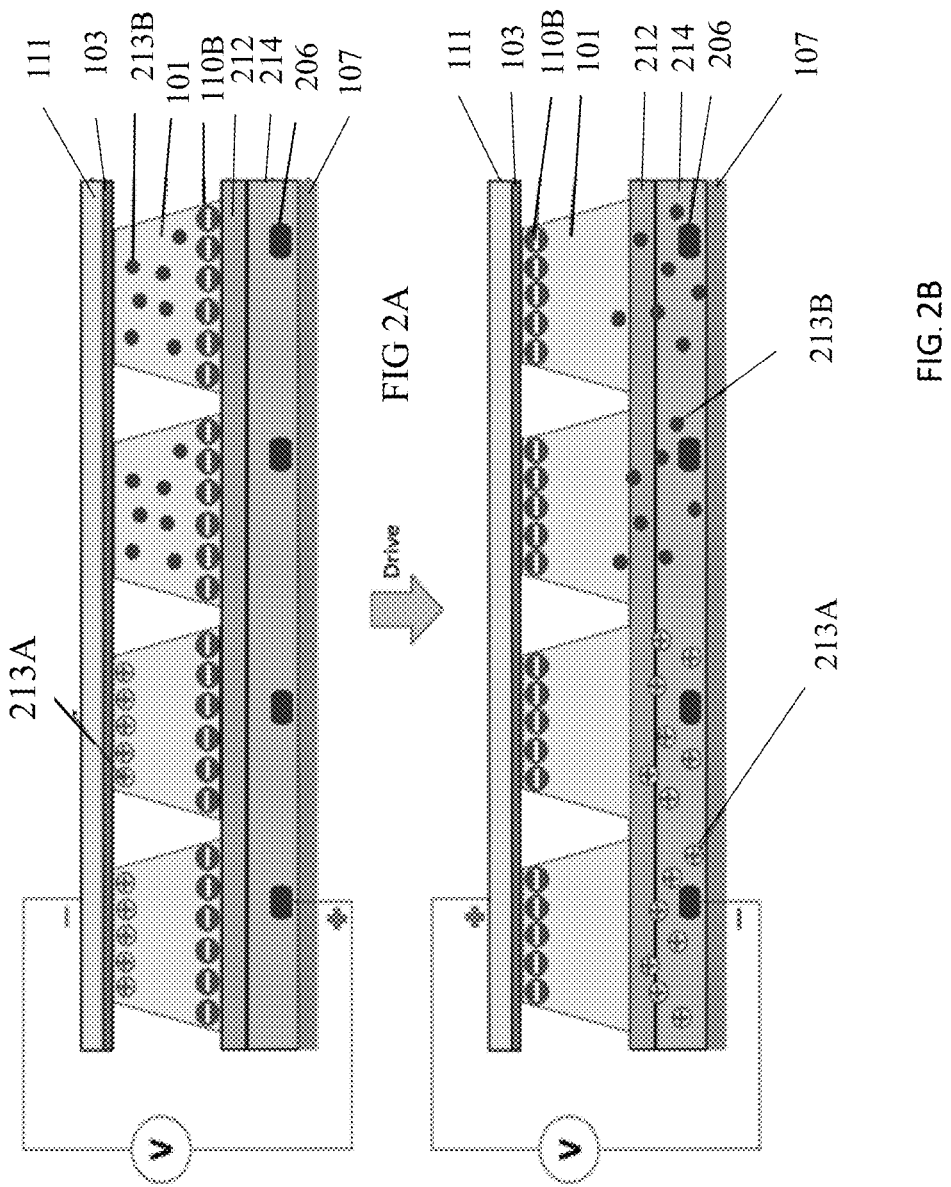

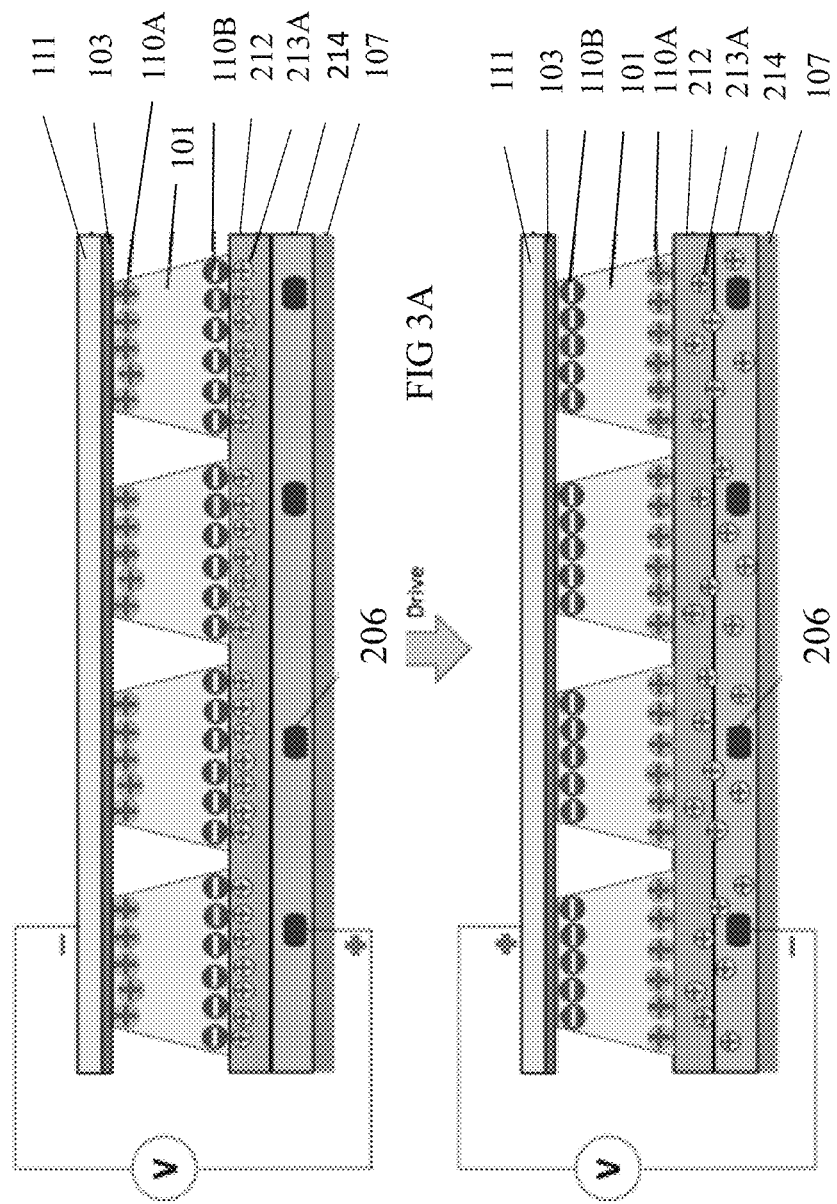

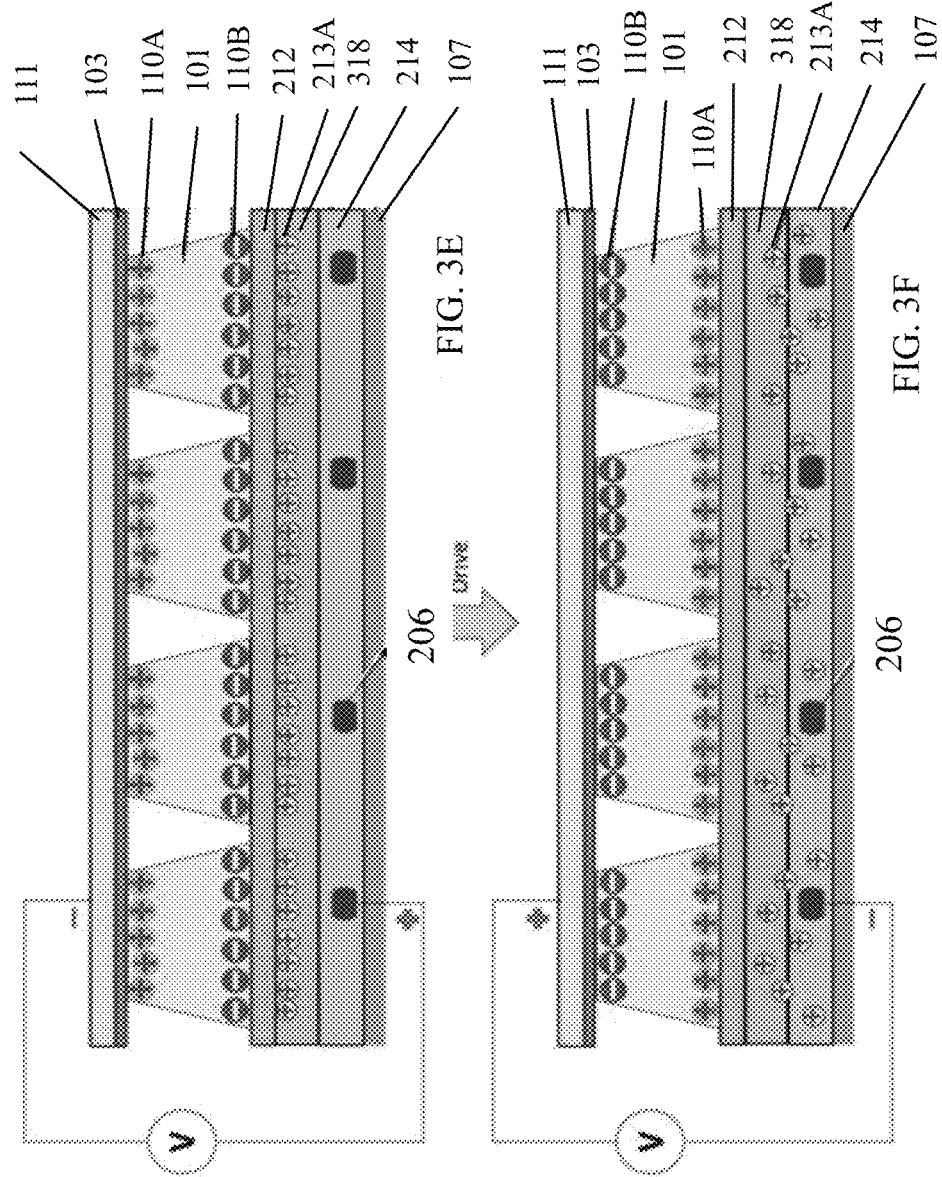

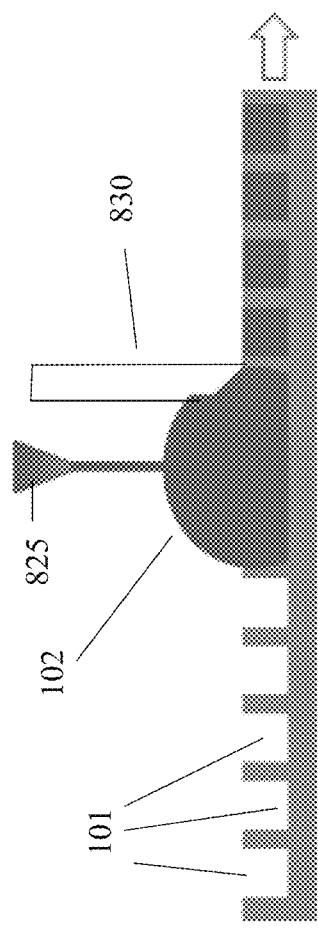
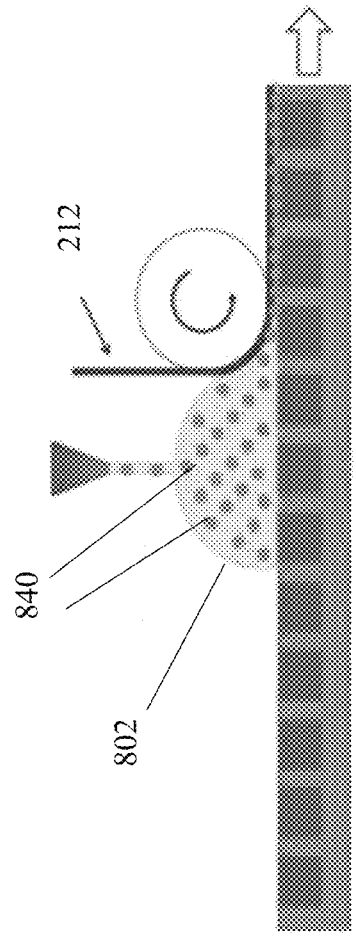
FIG. 8A
FIG. 8B

ELECTROPHORETIC ACTIVE DELIVERY SYSTEM INCLUDING POROUS CONDUCTIVE ELECTRODE LAYER

RELATED APPLICATIONS

This application claims priority to U.S. Provisional Patent Application No. 62/585,663, filed Nov. 14, 2017 which is incorporated by reference in its entirety, along with all other patents and patent applications disclosed herein.

BACKGROUND

Transdermal delivery of pharmaceutical agents has proven effective for drugs that are able to move across the skin barrier. For example, small amounts of nicotine can be delivered over extended periods with transdermal patches that suspend the nicotine in an ethylene vinyl acetate (EVA) copolymer. See, e.g., Nicoderm-CQ® by GlaxoSmithKline (Brentford, UK). Most of the commercially-available transdermal patches contain a matrix with only one drug, or a combination of drugs that are compatible for storage, such as oxycodone and tocopherol. See, e.g., TPM/Oxycodone patch from Phosphagenics, Ltd. (Melbourne, AU). Nonetheless, the efficacy of multi-component patches may degrade with time as the components interact. See, e.g., reports of crystallization in rotigotine transdermal patches (Nuepro®, UCB, Inc., Smyrna, Ga.).

Because there are a number of medications that are best administered in combination, there is a need for a simple (and inexpensive) delivery system that allows for the simultaneous delivery of multiple active components from the same transdermal system. Additionally, it would be beneficial if the delivery could be accomplished on demand sometime after the transdermal patch has been affixed to the skin.

SUMMARY

The invention addresses these needs by providing a transdermal delivery system whereby active molecules can be administered with an electric potential. The systems of the invention allow for the delivery of different types, different concentrations, and/or different volumes of active molecules from the same delivery system. The actives may be pharmaceutical compounds, vitamins, adjuvants, biologics, penetrants, vaccines, or genetic material (i.e., DNA or RNA). The actives may be water soluble or water insoluble.

Thus, in one aspect the invention is an active molecule delivery system including a plurality of microcells. The microcells may be square, round, or polygonal, such as a honeycomb structure. Each microcell includes an opening that is spanned by a porous conductive layer. The porous conductive layer may comprise, e.g., a conductive grid or mesh. The porous conductive layer may comprise a mat of conductive filaments, such as made from carbon, e.g., carbon nanotubes, silver, nickel, or gold. The porous conductive layer may comprise a porous conductive film, e.g., a film coated with graphite. The delivery system may additionally comprise a porous diffusion layer which may be constructed from a variety of materials, such acrylate, methacrylate, polycarbonate, polyvinyl alcohol, cellulose, poly (N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. The porous conductive layer and the porous diffusion layer may be separate layers or they may be integrated into a single layer. Typically, each microcell has a volume greater than 100 nL, and the porous diffusion layer has an average pore size of between 1 nm and 100 nm.

In one aspect the active molecule delivery system allows different actives or concentrations to be delivered on demand. Such systems may include a system of independently-addressable electrodes disposed adjacent to microcells but opposite to the porous conductive layer. The electrodes above and below the microcells can be used to cause the electrophoretic delivery of the active or to cause the motion of an electrophoretic particle away from a porous layer, thereby allowing the release of the desired active. In one embodiment, the system includes at least first and second microcells, wherein the first microcell includes a first active molecule and the second microcell includes a second active molecule, which is different from the first active molecule. In another embodiment, the system includes at least first and second microcells, wherein the first microcell includes a first concentration of an active molecule and the second microcell includes a second concentration of the active molecule, which is different from the first concentration. In another embodiment, the system includes at least first and second microcells, wherein the average pore size of the porous conductive layer over the opening of the first microcell is different from the average pore size of the porous diffusion layer over the opening of the second microcell. In addition to varying the type and concentration of active molecules, it is also possible to prepare a system including an active and another useful compound such as a vitamin, adjuvant, etc. Other combinations of active molecules, agents, and concentrations will be evident to one of skill in the art.

In some embodiments, an active molecule is distributed in a biocompatible non-polar liquid, such as an oil, such as vegetable, fruit, or nut oil. In other embodiments, the active molecules are distributed in an aqueous liquid, such as water or an aqueous buffer. The mixtures may also include charge control agents, surfactants, nutrients, and adjuvants. Typically, the active molecule is a pharmaceutical compound, however systems of the invention can be used to deliver hormones, nutraceuticals, proteins, nucleic acids, antibodies, or vaccines.

In some embodiments, the active molecule delivery system will include a separate sealing layer. The sealing layer typically is used to seal the openings of the microcells, and is located between the openings of the microcells and the porous conductive layer. The sealing layer may be, for example, methylcellulose, hydroxymethylcellulose, an acrylate, a methacrylate, a polycarbonate, a polyvinyl alcohol, cellulose, poly(N-isopropylacrylamide) (PNIPAAm), poly (lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene.

BRIEF DESCRIPTION OF THE DRAWINGS

FIGS. 2A and 2B illustrate an embodiment of an active molecule delivery system including a plurality of microcells including a conductive grid electrode and a porous diffusion layer. In the embodiment of FIGS. 2A and 2B, different microcells have different formulations, thus a mixture of actives is delivered when the driving polarity is switched;

FIGS. 3A and 3B illustrate an embodiment of an active molecule delivery system including a plurality of microcells including a conductive grid electrode, a porous diffusion layer, and a sealing layer including charged drug molecules. In the embodiment of FIGS. 3A and 3B, the charged drug molecules are delivered to the skin from the sealing layer;

FIGS. 3E and 3F illustrate an embodiment of an active molecule delivery system including a plurality of microcells including a conductive grid electrode, a porous diffusion layer, a sealing layer, and a separate drug-loading layer. The porous diffusion layer includes charged drug molecules. In the embodiment of FIGS. 3E and 3F, the charged drug molecules are delivered to the skin from the drug-loading layer;

In FIGS. 5C and 5D a combination of top and bottom exposure is used, allowing the walls in one lateral direction to be cured by top photomask exposure, and the walls in another lateral direction to be cured bottom exposure through the opaque base conductor film;

FIG. 7A shows a conductive grid adjacent to the openings of the microcells. FIG. 7B shows a mat of conductive filaments adjacent to the openings of the microcells. FIG. 7C shows a conductive porous film adjacent to the openings of the microcells;

FIG. 8A illustrates filling microcells with an active formulation;

FIG. 8B illustrates sealing microcells with a sealing layer additionally comprising an adjuvant.

DESCRIPTION

The invention provides an active molecule delivery system whereby active molecules can be released on demand and/or a variety of different active molecules can be delivered from the same system and/or different concentrations of active molecules can be delivered from the same system. The invention is well-suited for delivering pharmaceuticals to patients transdermally, however the invention may be used to deliver active ingredients, generally. For example, the invention can deliver tranquilizing agents to a horse during transport. The active delivery system includes a first electrode, a plurality of microcells, and a porous conductive layer. The microcells are filled with a medium including active molecules. The microcells include an opening, and the opening is spanned by the porous conductive layer. The microcell arrays may be loaded with different active ingredients, thereby providing a mechanism to deliver different, or complimentary, active ingredients on demand.

In addition to more conventional applications, such as transdermal delivery of pharmaceutical compounds, the active molecule delivery system may be the basis for delivering agricultural nutrients. The active molecule delivery systems can also be incorporated into the structural walls of smart packing. Such delivery systems makes it possible to have long term release of antioxidants into a package containing fresh vegetables. This "smart" packaging will dramatically improve the shelf life of certain foods, and it will only require the amount of antioxidant necessary to maintain freshness until the package is opened. Thus, the same packaging can be used for food that is distributed locally, across the country, or around the globe.

The invention also provides a system for simple and low cost delivery of "cocktails" of active molecules on demand. Such a delivery system may be used, for example, as an emergency delivery system for a person undergoing an allergic reaction. The system may include epinephrine, as well as antihistamines. The device can be applied and then triggered to cause the actives to be quickly passed through the skin. The system may be particularly effective as a back-up system for small children who may be exposed to life-threatening allergens while on a field trip, etc. A parent can affix the delivery system to the child with instructions to activate the device in the event of, e.g., a bee sting. Because the device is relatively simple, compliance with proper delivery protocols will be greater than, e.g., an epipen.

Figure 1:
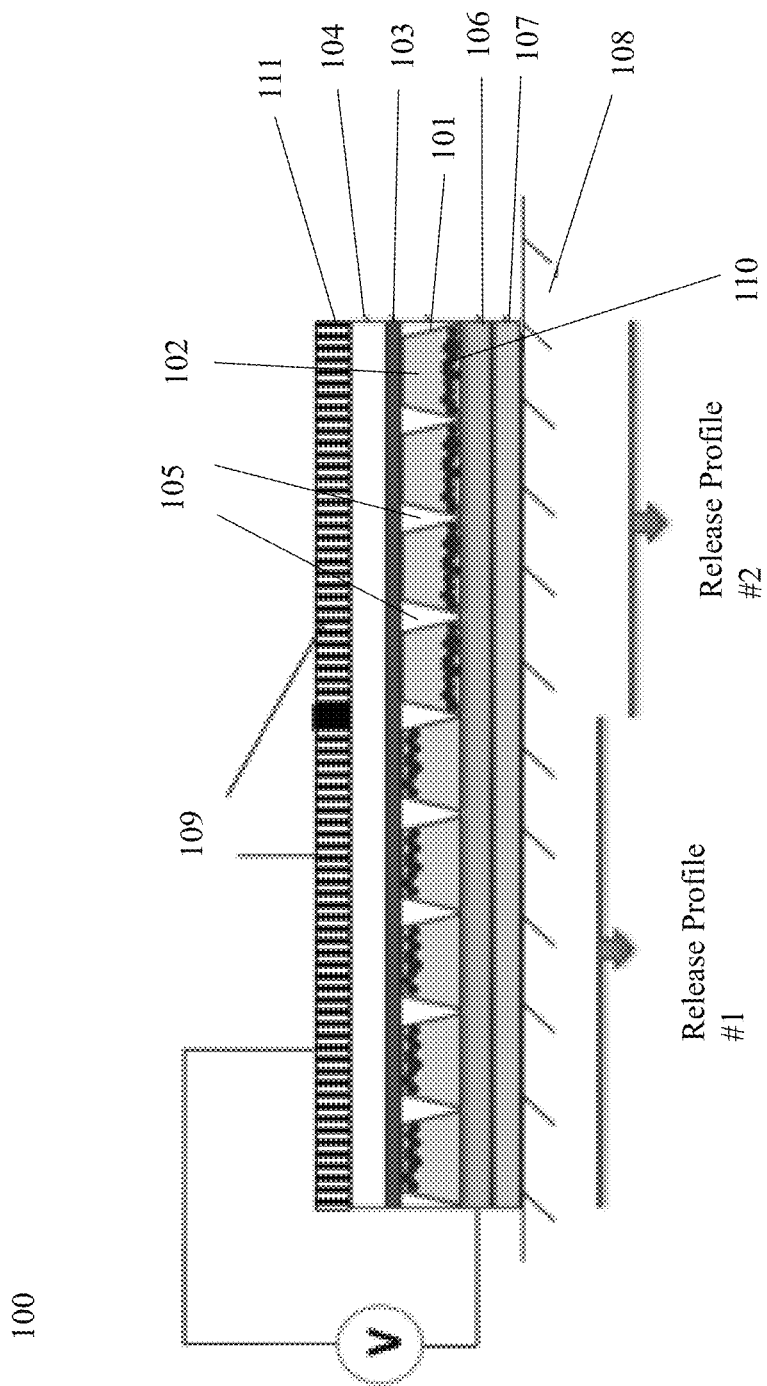
FIG. 1 illustrates an embodiment of an active molecule delivery system including a plurality of microcells including a porous conductive layer wherein different active molecules are included in different microcells. In the embodiment of FIG. 1, charged electrophoretic particles can be moved within the microcells to regulate the flow of the actives.

An overview of an active molecule delivery system 100 is shown in FIG. 1. The system includes a plurality of microcells 101, each microcell including an active formulation 102, which includes e.g., an active molecule, e.g., a pharmaceutical, e.g., a drug. Each microcell is part of an array that is formed from a polymer matrix, the construction of which is described in more detail below. The microcells 101 are typically coated with a primer 103, which reduces interactions between the microcell surfaces and the active formulation 102. The active molecule delivery system 100 will also typically include a protection layer 104 to provide structural support and protection against moisture ingress and physical interactions. The microcells 101 are defined by walls 105 that are at least 1 μm high, although they can be much higher depending upon the desired depth of the microcell. The microcells 101 may be arranged as squares, a honeycomb, circles, etc. The microcells 101 will have openings that are spanned by a porous conductive layer 106, which may comprise any biocompatible porous conductor, such as a grid, mesh, mat of conductive filaments, or a conductive porous film. The system may also include a porous diffusion layer, which may be constructed from a variety of natural or non-natural polymers, such as acrylates, methacrylates, polycarbonates, polyvinyl alcohols, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene. In some embodiments, the porous conductive layer 106 and the porous diffusion layer are integrated into the same layer. Often the system will additionally include an adhesive layer 107 that is also porous to the active molecule. The adhesive layer 107 assists in keeping the active molecule delivery system 100 adjacent to the surface. Any of the layers adjacent to the openings (e.g., porous diffusion, or adhesive) may comprise additional actives, such as adjuvants, such as penetration enhancers, that allow for combinations of materials to be delivered through the skin 108 simultaneously.

As shown in FIG. 1, different microcells may be addressed with different independent electrodes 109 at different times, giving rise to different release profiles within the same delivery system. Because the potential is controlled with the independent electrodes 109, it is possible to use a singular porous conductive layer 106 that spans the entire microcell array. Additionally, the electric field may be used to drive electrophoretic particles 110 which may regulate drug delivery by moving toward or adjacent to the porous layers. In other embodiments, the microcells 101 may include multiple different types of electrophoretic particles 110.

FIGS. 2A and 2B illustrate how the invention can be used to deliver more than one active and that active can be either charged or neutral. The actives can be loaded in the microcell layer 201 and/or the sealing layer 212 and/or the adhesive layer 107 and/or in a separate drug-loading layer (or layers) between the sealing 212 and adhesive 107 layers. The charged particles inside the microcell can be of only one polarity of electrical charge ("+" or "−") or contain both positively 110A and negatively charged 110B particles. The microcells 201 can also include different charged particles of the same charge polarity, but a different magnitude of charge. The porous conductive electrode 206 can be placed inside the adhesive layer 107 and/or inside sealing layer 212 and/or in a layer (or layers) between the sealing 212 and adhesive layer 107. The porous electrode 206 can also be at an interface between sealing layer 212 and adhesive layer 107 and/or at an interface between adhesive 107 and skin layer and/or at any interface when additional layer(s) is introduced between adhesive 107 and sealing layer 212.

As shown in FIG. 2A, a charged active 213A may be in a first portion of the microcells and a neutral active 213B may be in a second portion of the microcells. Meanwhile, both portions of the microcells can include charged particles 110B that are moved against the semi-porous sealing layer 212 with the correct biasing of the electrical potential between the top electrode 211 and the porous conductive layer 206. When the polarity is reversed, as shown in FIG. 2B, the charged particles 110B move toward the oppositely charged top electrode 211, thereby diminishing the restrictions to passage of the positively-charged 213A and neutral 213B actives through the semi-porous sealing layer 212, the porous conductive layer 206, and the porous diffusion layer 214. As shown in FIG. 2B, because the positively charged actives 213A are attracted to the polarity of the porous conductive layer 206, they move faster though the sealing 212/conductive 206/diffusion layers 214 than the neutral actives 213B. (The motion of the neutral active 213B is primarily a function of concentration gradients.)

Figure 3C:
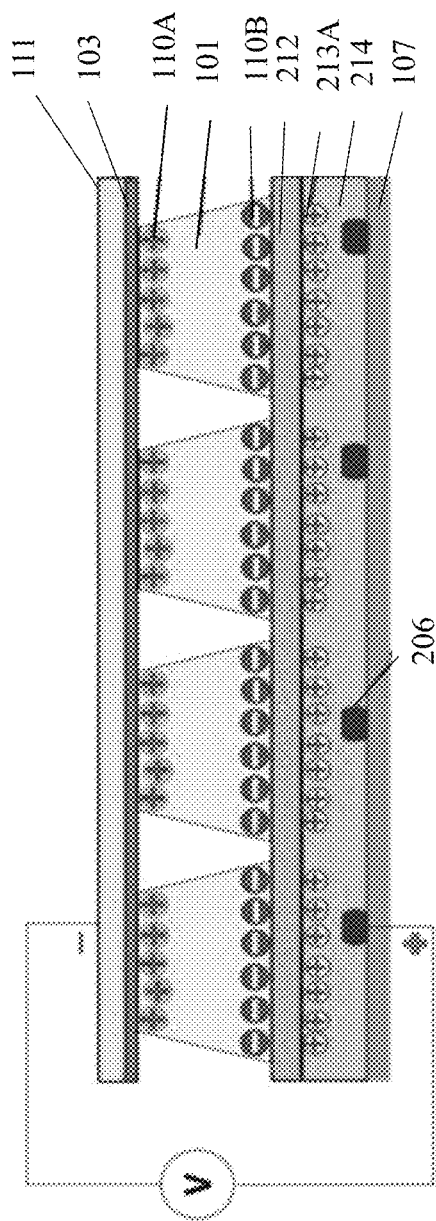
FIGS. 3C and 3D illustrate an embodiment of an active molecule delivery system including a plurality of microcells including a conductive grid electrode, a porous diffusion layer, and a sealing layer. The porous diffusion layer includes charged drug molecules. In the embodiment of FIGS. 3C and 3D, the charged drug molecules are delivered to the skin from the porous diffusion layer.
Figure 3D:
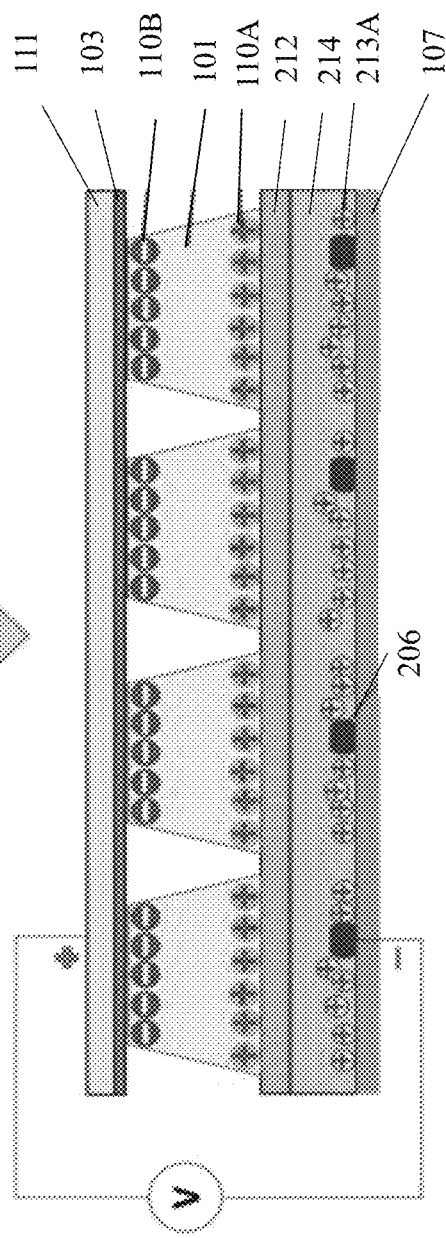

Additional functionality can be introduced into the active molecule delivery system by preloading one or more layers outside of the layer of microcells 301 with additional charged actives. The additional charged actives can be the same actives, or different actives, thereby allowing for baseline drug delivery or delivery of drug combinations. For example, the system may include charged actives 213A in a sealing layer 212, as shown in FIGS. 3A and 3B, or charged actives 213A in the porous diffusion layer 214, as shown in FIGS. 3C and 3D, or charged actives 213A in a separate drug-loading layer 318, as shown in FIGS. 3E and 3F. Furthermore, when two oppositely-charged particles 110A and 110B are included along with a light-transmissive top electrode 111, the delivery system can additionally function as an electrophoretic display that will visibly show the status of the device.

Of course, a variety of combinations are possible, and varying microcells might include pharmaceuticals, nutraceuticals, adjuvants, vitamins, penetrants, or vaccines. Furthermore, the arrangement of the microcells may not be distributed. Rather the microcells may be filled in clusters, which makes filling and sealing more straightforward. In other embodiments, smaller microcell arrays may be filled with the same medium, i.e., having the same active molecule at the same concentration, and then the smaller arrays assembled into a larger array to make a delivery system of the invention. All of these combinations may be further augmented with the addition of one or more layers that includes additional pharmaceuticals, nutraceuticals, adjuvants, vitamins, penetrants, or vaccines.

Techniques for Constructing Microcells.

Figure 4:
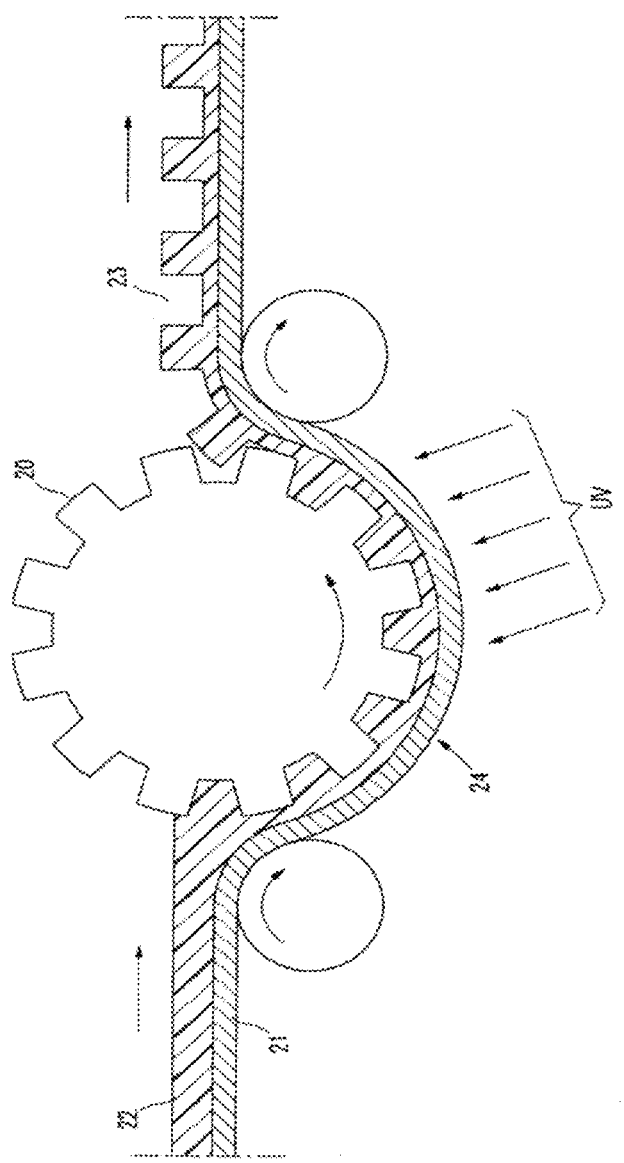
FIG. 4 shows a method for making microcells for the invention using a roll-to-roll process.

Microcells may be formed either in a batchwise process or in a continuous roll-to-roll process as disclosed in U.S. Pat. No. 6,933,098. The latter offers a continuous, low cost, high throughput manufacturing technology for production of compartments for use in a variety of applications including active molecule delivery and electrophoretic displays. Microcell arrays suitable for use with the invention can be created with microembossing, as illustrated in FIG. 4. A male mold 20 may be placed either above the web 24, as shown in FIG. 4, or below the web 24 (not shown) however alternative arrangements are possible. See U.S. Pat. No. 7,715,088, which is incorporated herein by reference in its entirety. A conductive substrate may be constructed by forming a conductor film 21 on polymer substrate that becomes the backing for a device. A composition comprising a thermoplastic, thermoset, or a precursor thereof 22 is then coated on the conductor film. The thermoplastic or thermoset precursor layer is embossed at a temperature higher than the glass transition temperature of the thermoplastics or thermoset precursor layer by the male mold in the form of a roller, plate or belt.

The thermoplastic or thermoset precursor for the preparation of the microcells may be multifunctional acrylate or methacrylate, vinyl ether, epoxide and oligomers or polymers thereof, and the like. A combination of multifunctional epoxide and multifunctional acrylate is also very useful to achieve desirable physico-mechanical properties. A crosslinkable oligomer imparting flexibility, such as urethane acrylate or polyester acrylate, may be added to improve the flexure resistance of the embossed microcells. The composition may contain polymer, oligomer, monomer and additives or only oligomer, monomer and additives. The glass transition temperatures (or $T_g$) for this class of materials usually range from about −70° C. to about 150° C., preferably from about −20° C. to about 50° C. The microembossing process is typically carried out at a temperature higher than the $T_g$. A heated male mold or a heated housing substrate against which the mold presses may be used to control the microembossing temperature and pressure.

As shown in FIG. 4, the mold is released during or after the precursor layer is hardened to reveal an array of microcells 23. The hardening of the precursor layer may be accomplished by cooling, solvent evaporation, cross-linking by radiation, heat or moisture. If the curing of the thermoset precursor is accomplished by UV radiation, UV may radiate onto the transparent conductor film from the bottom or the top of the web as shown in the two figures. Alternatively, UV lamps may be placed inside the mold. In this case, the mold must be transparent to allow the UV light to radiate through the pre-patterned male mold on to the thermoset precursor layer. A male mold may be prepared by any appropriate method, such as a diamond turn process or a photoresist process followed by either etching or electroplating. A master template for the male mold may be manufactured by any appropriate method, such as electroplating. With electroplating, a glass base is sputtered with a thin layer (typically 3000 Å) of a seed metal such as chrome inconel. The mold is then coated with a layer of photoresist and exposed to UV. A mask is placed between the UV and the layer of photoresist. The exposed areas of the photoresist become hardened. The unexposed areas are then removed by washing them with an appropriate solvent. The remaining hardened photoresist is dried and sputtered again with a thin layer of seed metal. The master is then ready for electroforming. A typical material used for electroforming is nickel cobalt. Alternatively, the master can be made of nickel by electroforming or electroless nickel deposition. The floor of the mold is typically between about 50 to 400 microns. The master can also be made using other microengineering techniques including e-beam writing, dry etching, chemical etching, laser writing or laser interference as described in "Replication techniques for micro-optics", SPIE Proc. Vol. 3099, pp. 76-82 (1997). Alternatively, the mold can be made by photomachining using plastics, ceramics or metals.

Prior to applying a UV curable resin composition, the mold may be treated with a mold release to aid in the demolding process. The UV curable resin may be degassed prior to dispensing and may optionally contain a solvent. The solvent, if present, readily evaporates. The UV curable resin is dispensed by any appropriate means such as, coating, dipping, pouring or the like, over the male mold. The dispenser may be moving or stationary. A conductor film is overlaid the UV curable resin. Pressure may be applied, if necessary, to ensure proper bonding between the resin and the plastic and to control the thickness of the floor of the microcells. The pressure may be applied using a laminating roller, vacuum molding, press device or any other like means. If the male mold is metallic and opaque, the plastic substrate is typically transparent to the actinic radiation used to cure the resin. Conversely, the male mold can be transparent and the plastic substrate can be opaque to the actinic radiation. To obtain good transfer of the molded features onto the transfer sheet, the conductor film needs to have good adhesion to the UV curable resin which should have a good release property against the mold surface.

Photolithography.

Figure 5A:
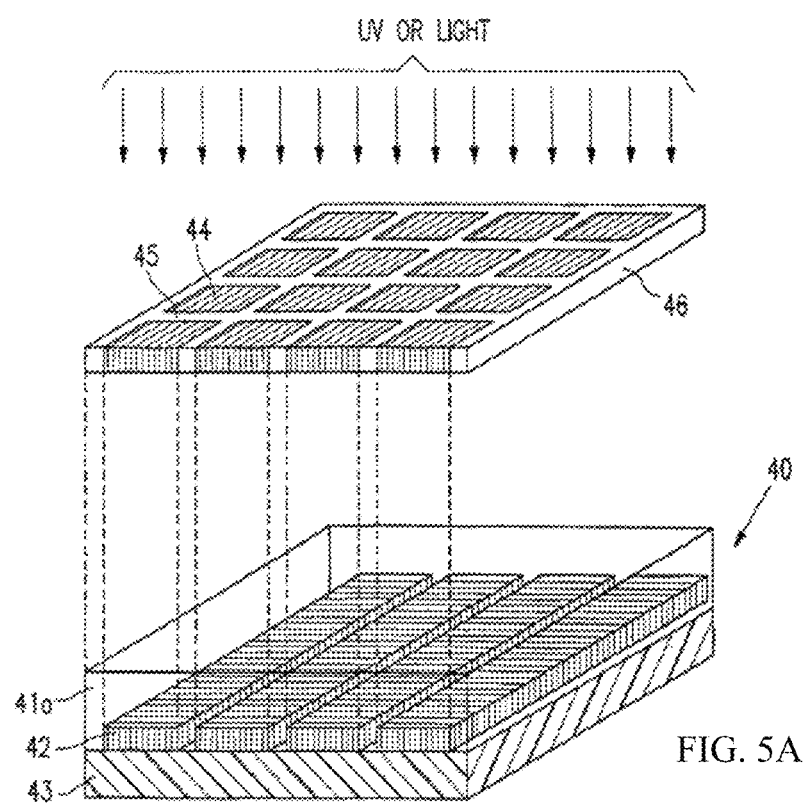
FIGS. 5A and 5B detail the production of microcells for an active molecule delivery system using photolithographic exposure through a photomask of a conductor film coated with a thermoset precursor.
Figure 5B:
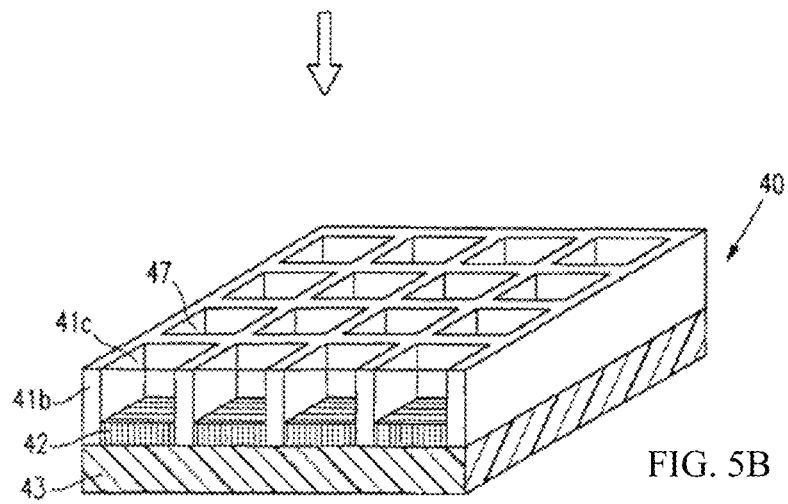

Microcells can also be produced using photolithography. Photolithographic processes for fabricating a microcell array are illustrated in FIGS. 5A and 5B. As shown in FIGS. 5A and 5B, the microcell array 40 may be prepared by exposure of a radiation curable material 41a coated by known methods onto a conductor electrode film 42 to UV light (or alternatively other forms of radiation, electron beams and the like) through a mask 46 to form walls 41b corresponding to the image projected through the mask 46. The base conductor film 42 is preferably mounted on a supportive substrate base web 43, which may comprise a plastic material.

In the photomask 46 in FIG. 5A, the dark squares 44 represent the opaque area and the space between the dark squares represents the transparent area 45 of the mask 46. The UV radiates through the transparent area 45 onto the radiation curable material 41a. The exposure is preferably performed directly onto the radiation curable material 41a, i.e., the UV does not pass through the substrate 43 or base conductor 42 (top exposure). For this reason, neither the substrate 43, nor the conductor 42, needs to be transparent to the UV or other radiation wavelengths employed.

As shown in FIG. 5B, the exposed areas 41b become hardened and the unexposed areas (protected by the opaque area 44 of the mask 46) are then removed by an appropriate solvent or developer to form the microcells 47. The solvent or developer is selected from those commonly used for dissolving or reducing the viscosity of radiation curable materials such as methylethylketone (MEK), toluene, acetone, isopropanol or the like. The preparation of the microcells may be similarly accomplished by placing a photomask underneath the conductor film/substrate support web and in this case the UV light radiates through the photomask from the bottom and the substrate needs to be transparent to radiation.

Imagewise Exposure.

Figure 5D:
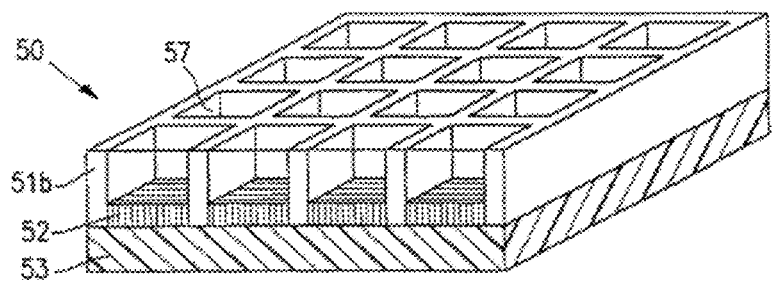
FIGS. 5C and 5D detail an alternate embodiment in which microcells for an active molecule delivery system are fabricated using photolithography.
Figure 5C:
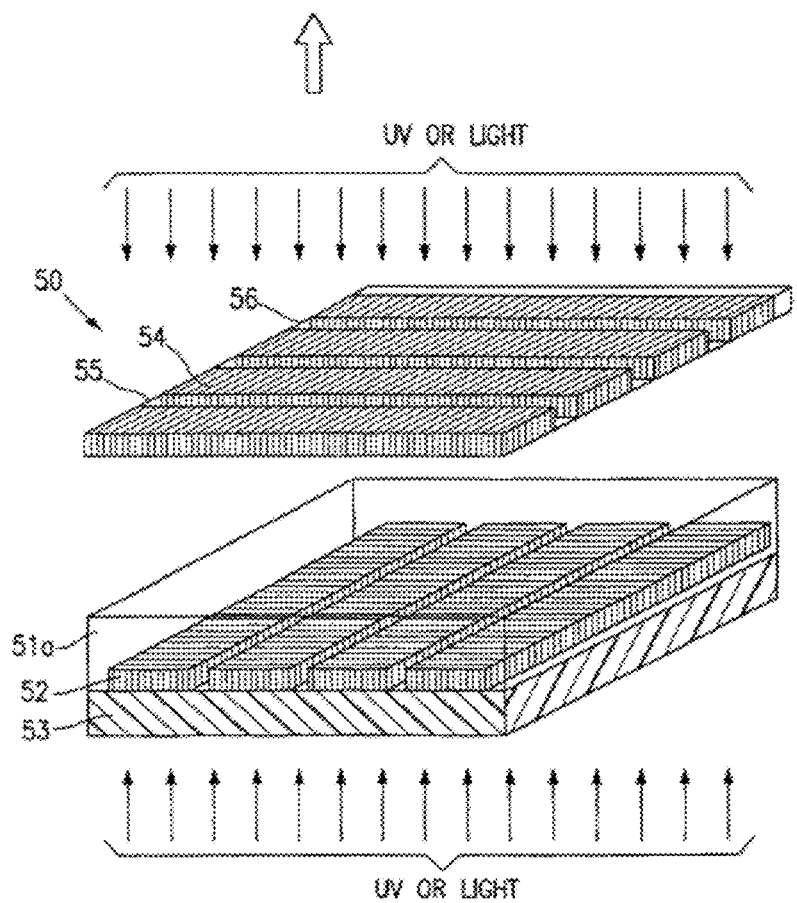

Still another alternative method for the preparation of the microcell array of the invention by imagewise exposure is illustrated in FIGS. 5C and 5D. When opaque conductor lines are used, the conductor lines can be used as the photomask for the exposure from the bottom. Durable microcell walls are formed by additional exposure from the top through a second photomask having opaque lines perpendicular to the conductor lines. FIG. 5C illustrates the use of both the top and bottom exposure principles to produce the microcell array 50 of the invention. The base conductor film 52 is opaque and line-patterned. The radiation curable material 51a, which is coated on the base conductor 52 and substrate 53, is exposed from the bottom through the conductor line pattern 52 which serves as the first photomask. A second exposure is performed from the "top" side through the second photomask 56 having a line pattern perpendicular to the conductor lines 52. The spaces 55 between the lines 54 are substantially transparent to the UV light. In this process, the wall material 51b is cured from the bottom up in one lateral orientation, and cured from the top down in the perpendicular direction, joining to form an integral microcell 57. As shown in FIG. 5D, the unexposed area is then removed by a solvent or developer as described above to reveal the microcells 57. The technique described in FIGS. 5C and 5D thus allow the different walls to be constructed with different porosity, as needed for the embodiment illustrated in FIG. 3.

The microcells may be constructed from thermoplastic elastomers, which have good compatibility with the microcells and do not interact with the electrophoretic media. Examples of useful thermoplastic elastomers include ABA, and (AB)n type of di-block, tri-block, and multi-block copolymers wherein A is styrene, α-methylstyrene, ethylene, propylene or norbornene; B is butadiene, isoprene, ethylene, propylene, butylene, dimethylsiloxane or propylene sulfide; and A and B cannot be the same in the formula. The number, n, is ≥1, preferably 1-10. Particularly useful are di-block or tri-block copolymers of styrene or ox-methyl-styrene such as SB (poly(styrene-b-butadiene)), SBS (poly(styrene-b-butadiene-b-styrene)), SIS (poly(styrene-b-isoprene-b-styrene)), SEBS (poly(styrene-b-ethylene/butylenes-b-stylene)) poly(styrene-b-dimethylsiloxane-b-styrene), poly((α-methylstyrene-b-isoprene), poly(α-methylstyrene-b-isoprene-b-α-methylstyrene), poly(α-methylstyrene-b-propylene sulfide-b-α-methylstyrene), poly(α-methylstyrene-b-dimethylsiloxane-b-α-methylstyrene). Commercially available styrene block copolymers such as Kraton D and G series (from Kraton Polymer, Houston, Tex.) are particularly useful. Crystalline rubbers such as poly(ethylene-co-propylene-co-5-methylene-2-norbornene) or EPDM (ethylene-propylene-diene terpolymer)

rubbers such as Vistalon 6505 (from Exxon Mobil, Houston, Tex.) and their grafted copolymers have also been found very useful.

The thermoplastic elastomers may be dissolved in a solvent or solvent mixture which is immiscible with the display fluid in the microcells and exhibits a specific gravity less than that of the display fluid. Low surface tension solvents are preferred for the overcoating composition because of their better wetting properties over the microcell walls and the electrophoretic fluid. Solvents or solvent mixtures having a surface tension lower than 35 dyne/cm are preferred. A surface tension of lower than 30 dyne/cm is more preferred. Suitable solvents include alkanes (preferably $C_{6-12}$ alkanes such as heptane, octane or Isopar solvents from Exxon Chemical Company, nonane, decane and their isomers), cycloalkanes (preferably $C_{6-12}$ cycloalkanes such as cyclohexane and decalin and the like), alkylbezenes (preferably mono- or di-$C_{1-6}$ alkyl benzenes such as toluene, xylene and the like), alkyl esters (preferably $C_{2-5}$ alkyl esters such as ethyl acetate, isobutyl acetate and the like) and $C_{3-5}$ alkyl alcohols (such as isopropanol and the like and their isomers). Mixtures of alkylbenzene and alkane are particularly useful.

In addition to polymer additives, the polymer mixtures may also include wetting agents (surfactants). Wetting agents (such as the FC surfactants from 3M Company, Zonyl fluorosurfactants from DuPont, fluoroacrylates, fluoromethacrylates, fluoro-substituted long chain alcohols, perfluoro-substituted long chain carboxylic acids and their derivatives, and Silwet silicone surfactants from OSi, Greenwich, Conn.) may also be included in the composition to improve the adhesion of the sealant to the microcells and provide a more flexible coating process. Other ingredients including cross-linking agents (e.g., bisazides such as 4,4'-diazidodiphenylmethane and 2,6-di-(4'-azidobenzal)-4-methylcyclohexanone), vulcanizers (e.g., 2-benzothiazolyl disulfide and tetramethylthiuram disulfide), multifunctional monomers or oligomers (e.g., hexanediol, diacrylates, trimethylolpropane, triacrylate, divinylbenzene, diallylphthalene), thermal initiators (e.g., dilauroryl peroxide, benzoyl peroxide) and photoinitiators (e.g., isopropyl thioxanthone (ITX), Irgacure 651 and Irgacure 369 from Ciba-Geigy) are also highly useful to enhance the physico-mechanical properties of the sealing layer by crosslinking or polymerization reactions during or after the overcoating process.

After the microcells are produced, they are filled with appropriate mixtures of active molecules. The microcell array 60 may be prepared by any of the methods described above. As shown in cross-section in FIGS. 6A-6D, the microcell walls 61 extend upward from the substrate 63 to form the open cells. The microcells may include a primer layer 62 to passivate the mixture and keep the microcell material from interacting with the mixture containing the actives 65. Prior to filling, the microcell array 60 may be cleaned and sterilized to assure that the active molecules are not compromised prior to use.

Figure 6A:
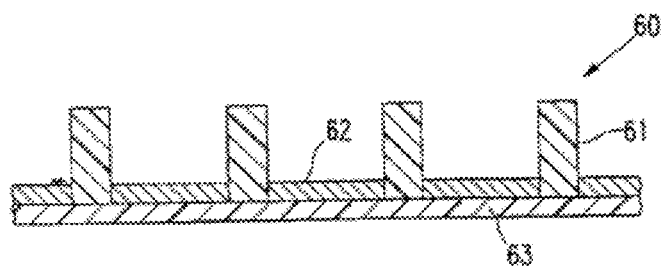
FIGS. 6A-6D illustrate the steps of filling and sealing an array of microcells to be used in an active molecule delivery system.
Figure 6B:
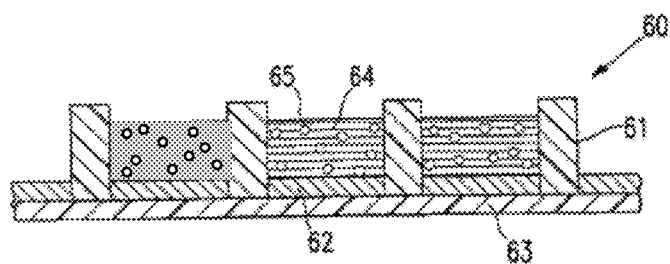

The microcells are next filled with a mixture 64 including active molecules 65. As shown in FIG. 6B, different microcells may include different actives. The microcells 60 are preferably partially filled to prevent overflow and the unintentional mixing of active ingredients. In systems for delivering hydrophobic active molecules, the mixture may be based upon a biocompatible oil or some other biocompatible hydrophobic carrier. For example, the mixture may comprise a vegetable, fruit, or nut oil. In other embodiments, silicone oils may be used. In systems for delivering hydrophilic active molecules, the mixture may be based upon water or another aqueous medium such as phosphate buffer. The mixture need not be a liquid, however, as hydrogels and other matrices may be suitable to deliver the active molecules 65.

The microcells may be filled using a variety of techniques. In some embodiments, where a large number of neighboring microcells are to be filled with an identical mixture, blade coating may be used to fill the microcells to the depth of the microcell walls 61. In other embodiments, where a variety of different mixtures are to be filled in a variety of nearby microcell, inkjet-type microinjection can be used to fill the microcells. In yet other embodiments, microneedle arrays may be used to fill an array of microcells with the correct mixtures. The filling may be done in a one-step, or a multistep process. For example, all of the cells may be partially filled with an amount of solvent. The partially filled microcells are then filled with a second mixture including the one or more active molecules to be delivered.

Figure 6C:
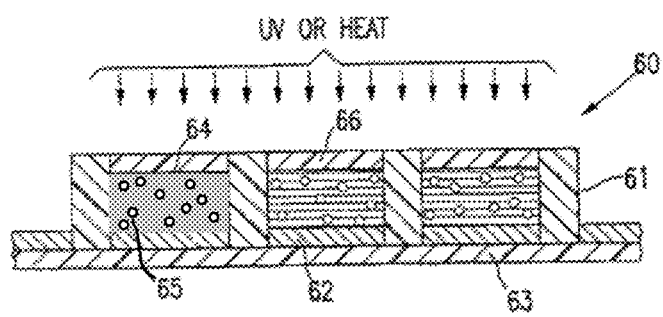
Figure 6D:
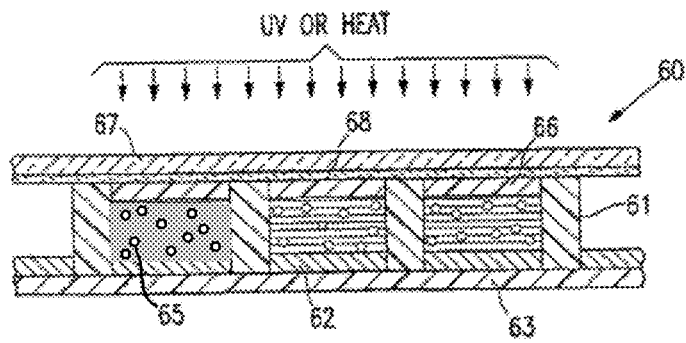

As shown in FIG. 6C, after filling, the microcells are sealed by applying a polymer 66 that becomes the porous diffusion layer. In some embodiments, the sealing process may involve exposure to heat, dry hot air, or UV radiation. In most embodiments the polymer 66 will be compatible with the mixture 64, but not dissolved by the solvent of the mixture 64. The polymer 66 will also be biocompatible and selected to adhere to the sides or tops of the microcell walls 61. A suitable biocompatible adhesive for the porous diffusion layer is a phenethylamine mixture, such as described in U.S. patent application Ser. No. 15/336,841, filed Oct. 30, 2016 and titled "Method for Sealing Microcell Containers with Phenethylamine Mixtures," which is incorporated herein by reference in its entirety. Accordingly, the final microcell structure is mostly impervious to leaks and able to withstand flexing without delamination of the porous diffusion layer.

In alternate embodiments, a variety of individual microcells may be filled with the desired mixture by using iterative photolithography. The process typically includes coating an array of empty microcells with a layer of positively working photoresist, selectively opening a certain number of the microcells by imagewise exposing the positive photoresist, followed by developing the photoresist, filling the opened microcells with the desired mixture, and sealing the filled microcells by a sealing process. These steps may be repeated to create sealed microcells filled with other mixtures. This procedure allows for the formation of large sheets of microcells having the desired ratio of mixtures or concentrations.

After the microcells 60 are filled, the sealed array may be laminated with a finishing layer 68 that is also porous to the active molecules, preferably by pre-coating the finishing layer 68 with an adhesive layer which may be a pressure sensitive adhesive, a hot melt adhesive, or a heat, moisture, or radiation curable adhesive. The laminate adhesive may be post-cured by radiation such as UV through the top conductor film if the latter is transparent to the radiation. In some embodiments, a biocompatible adhesive 67 is then laminated to the assembly. The biocompatible adhesive 67 will allow active molecules to pass through while keeping the device mobile on a user. Suitable biocompatible adhesives are available from 3M (Minneapolis, Minn.).

In order for the porous conductive layer to drive all the charged particles inside microcell, the sealing layer will preferred to have lower electrical resistivity than the EPD requirement, preferably less than $10^9$ ohm·cm. If the resistivity of the sealing layer is higher, the local field strength within the microcells may not be sufficient to move the charge particles away from the porous diffusion layer, etc.

When the sealing resistance is low, the fringing field is wide enough to cover the areas without electrodes and therefore all of the charged particles inside microcell will be driven.

Once the delivery system has been constructed, it may be covered with an encapsulating backing to provide protection against physical shock. The encapsulating backing may also include adhesives to make sure that the active molecule delivery system stays affixed, e.g., to a patient's back. The encapsulating backing may also include aesthetic coloring or fun designs for children. The sealing layer is semi-porous in most applications, that is, the sealing layer to form a barrier that prevents any fluid contained within the microcell from escaping while the actives are allowed to pass. The sealing layer 78 may be constructed from any of the materials listed above with respect to the porous diffusion layer. In addition, the sealing layer can also be constructed from poly(vinylpyrrolidone), hydroxymethylcellulose, or polyvinyl alcohols.

Porous Conductive Layer.

Figures 7A, 7B, 7C:
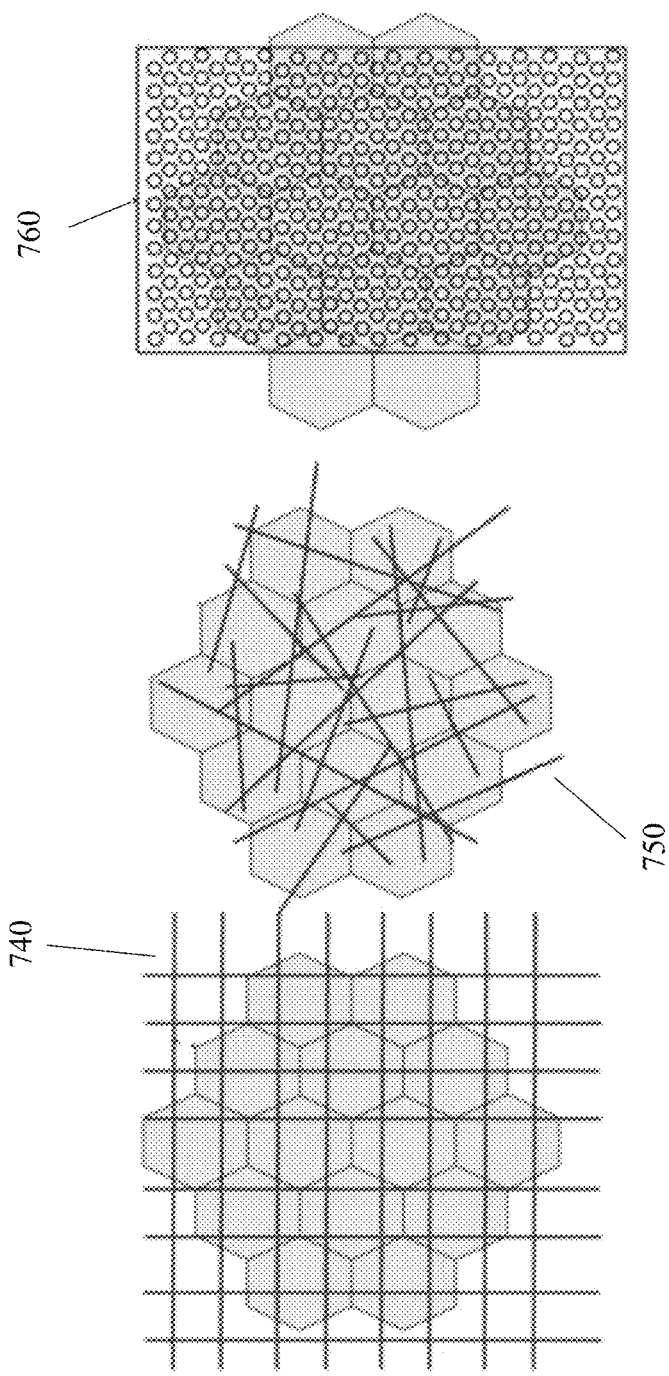
FIGS. 7A, 7B, and 7C illustrate alternative embodiments of a porous conductive layer.

A variety of constructions are suitable as porous conductive layers. For example, the porous electrode can be a conductive metal mesh or grid 740 as shown in FIG. 7A. Alternatively, fabric or nylon bandages can be coated/infiltrated with biocompatible conductive material, such as copper, silver, or conductive polymers, thereby allowing the device to flex. The porous electrode can also be made out of a mat of conductive filaments 750, fibers, and/or platelets, as shown in FIG. 7B. The conductive network shows an irregular shape compared to the metal mesh or polymer fabric network, however, the overall bias should be maintained if the mat has a sufficient density of conducting components. The mat can be constructed from, e.g., silver nanowires, carbon nanotubes, nickel nanowires, gold nanowires, spun gold, graphene platelets, or combinations thereof. In some embodiments, the conductive filaments will incorporated into polymer solution, dispersion, or slurry to make a coating that is then dried to create a porous conductive layer. The conductive network is formed after drying but the metal mesh or polymer fabric normally have a pre-defined pattern. One example for the irregular conductive network is to use silver nanowire or carbon nanotubes, which have large aspect ratios. In other embodiments, the porous conductive layer may comprise a continuous film of porous material 760 that is fabricated from conductive materials, such as conductive polymers, or the film is coated with a conductive material, such as a metal, or a conductive polymer, or graphite. In one embodiment, the porous conductive film may be graphite-coated poly(ethylene terephthalate) or cellulose coated with carbon black.

An additional benefit of using a continuous film of porous conductive material is that the active delivery devices can be manufactured in a roll-to-roll process, as shown in FIGS. 8A and 8B. After a microcell assembly is constructed as described above, the microcells 101 are filled with an active formulation 102 by dispensing the formulation atop the microcells 101 and removing the excess, e.g., with a blade 830, as shown in FIG. 8A. This process can be done continuously, as the microcell layer is moved with respect to the formulation dispenser 825. At a second stage, shown in FIG. 8B, the formulation 802 is sealed with a sealing layer 212, which may optionally include another active (i.e., the adjuvant 840 shown in FIG. 8B). The sealing layer 212 may be UV cured, or it may be cured with temperature. At the same time that the sealing layer 212 is added, the conductive porous film is rolled atop the filled microcells, resulting in a roll of active delivery system. In one embodiment, the top electrode may also be flexible and applied at an earlier stage to the microcell layer. More commonly, the top electrode will be added at a later step by adhering the filled and sealed layers to the top electrode, which may be, e.g., an independently addressable electrode, such as an array of segmented electrodes or an active matrix that is controlled with thin film transistors.

Thus the invention provides for an active molecule delivery system including a plurality of microcells. The microcells may include differing active molecules, or differing concentrations of active molecules. The microcells include an opening that is spanned by a porous conductive layer in addition to a porous diffusion layer. This disclosure is not limiting, and other modifications to the invention, not described, but self-evident to one of skill in the art, are to be included in the scope of the invention.

The invention claimed is:

1. An active molecule delivery system comprising:
a top electrode;
a plurality of microcells containing an active formulation and having an opening, the active formulation comprising active molecules and charged particles that move in the presence of an electric field;
a porous conductive layer, wherein the plurality of microcells are disposed between the top electrode and the porous conductive layer, and oriented so that the porous conductive layer is adjacent the microcell openings; and
a voltage source coupled to the top electrode and the porous conductive layer;
wherein the electric field is applied by the voltage source and causes a motion of the charged particles away from the porous conductive layer, thereby allowing delivery of the active molecules via the porous conductive layer.

2. The active molecule delivery system of claim 1, further comprising a sealing layer between the openings of the microcells and the porous conductive layer.

3. The active molecule delivery system of claim 1, further comprising a porous diffusion layer.

4. The active molecule delivery system of claim 3, further comprising an adhesive layer adjacent to the porous diffusion layer.

5. The active molecule delivery system of claim 4, further comprising a backing layer adjacent to the adhesive layer.

6. The active molecule delivery system of claim 3, wherein the porous diffusion layer comprises an acrylate, a methacrylate, a polycarbonate, a polyvinyl alcohol, cellulose, poly(N-isopropylacrylamide) (PNIPAAm), poly(lactic-co-glycolic acid) (PLGA), polyvinylidene chloride, acrylonitrile, amorphous nylon, oriented polyester, terephthalate, polyvinyl chloride, polyethylene, polypropylene, polybutylene, polyisobutylene, or polystyrene.

7. The active molecule delivery system of claim 3, wherein the porous diffusion layer has an average pore size of between 10 nm and 100 μm.

8. The active molecule delivery system of claim 1, wherein the active formulation includes a pharmaceutical compound.

9. The active molecule delivery system of claim 1, wherein the active formulation includes an active and a biocompatible non-polar liquid.

10. The active molecule delivery system of claim 1, wherein the active formulation includes an active and an aqueous liquid.

11. The active molecule delivery system of claim 1, wherein each of the plurality of microcells has a volume greater than 100 nL.

12. The active molecule delivery system of claim 1, wherein the plurality of microcells includes a first microcell, containing the active formulation, and a second microcell, containing a second active formulation.

13. The active molecule delivery system of claim 1, wherein the plurality of microcells includes a first microcell, containing a first concentration of the active formulation, and a second microcell, containing a second concentration of the active formulation.

14. The active molecule delivery system of claim 1, further comprising a second electrode, adjacent to the top electrode, and located on the same side of the plurality of microcells as the top electrode.

15. The active molecule delivery system of claim 14, wherein the top electrode and the second electrode are independently addressable.

16. The active molecule delivery system of claim 1, wherein the porous conductive layer comprises a conductive mesh.

17. The active molecule delivery system of claim 1, wherein the porous conductive layer comprises a mat of conductive filaments.

18. The active molecule delivery system of claim 1, wherein the porous conductive layer comprises a conductive porous film.

19. The active molecule delivery system of claim 18, wherein the conductive porous film is coated with graphite.

* * * * *